United States Patent
Okazaki

(10) Patent No.: US 7,369,220 B2
(45) Date of Patent: May 6, 2008

(54) MEASURING APPARATUS

(75) Inventor: Kenya Okazaki, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/643,616

(22) Filed: Dec. 21, 2006

(65) Prior Publication Data

US 2007/0103687 A1 May 10, 2007

Related U.S. Application Data

(63) Continuation of application No. PCT/JP2005/011293, filed on Jun. 20, 2005.

(30) Foreign Application Priority Data

Jun. 21, 2004 (JP) ............................. 2004-182510

(51) Int. Cl.
*G01J 1/00* (2006.01)
(52) U.S. Cl. ...................... 356/123; 356/244
(58) Field of Classification Search ............... 356/624, 356/123, 317–318, 417; 250/201.4, 201.6, 250/201.7, 201.8
See application file for complete search history.

(56) References Cited

U.S. PATENT DOCUMENTS 6,071,748 A 6/2000 Modlin et al.

6,441,894 B1 * 8/2002 Manian et al. ............... 356/123

FOREIGN PATENT DOCUMENTS

| JP | 02-59963 | 12/1990 |
|---|---|---|
| JP | 11-502608 | 3/1999 |
| JP | 2002-228659 | 8/2002 |
| JP | 2002-541430 | 12/2002 |
| JP | 2002-542480 | 12/2002 |
| JP | 2003-526814 | 9/2003 |
| JP | 2005-17185 | 1/2005 |
| JP | 2005-98747 | 4/2005 |

\* cited by examiner

*Primary Examiner*—Layla G. Lauchman
*Assistant Examiner*—Juan D Valentin, II
(74) *Attorney, Agent, or Firm*—Scully, Scott, Murphy & Presser, P.C.

(57) ABSTRACT

A measuring apparatus which applies light, emitted from a light source, to a sample contained in a container, and detects light emitted from the sample to measure physical or chemical properties of the sample, includes a measuring optical system which measures the sample, and a position detection optical system which detects the position of the bottom of the container.

12 Claims, 14 Drawing Sheets

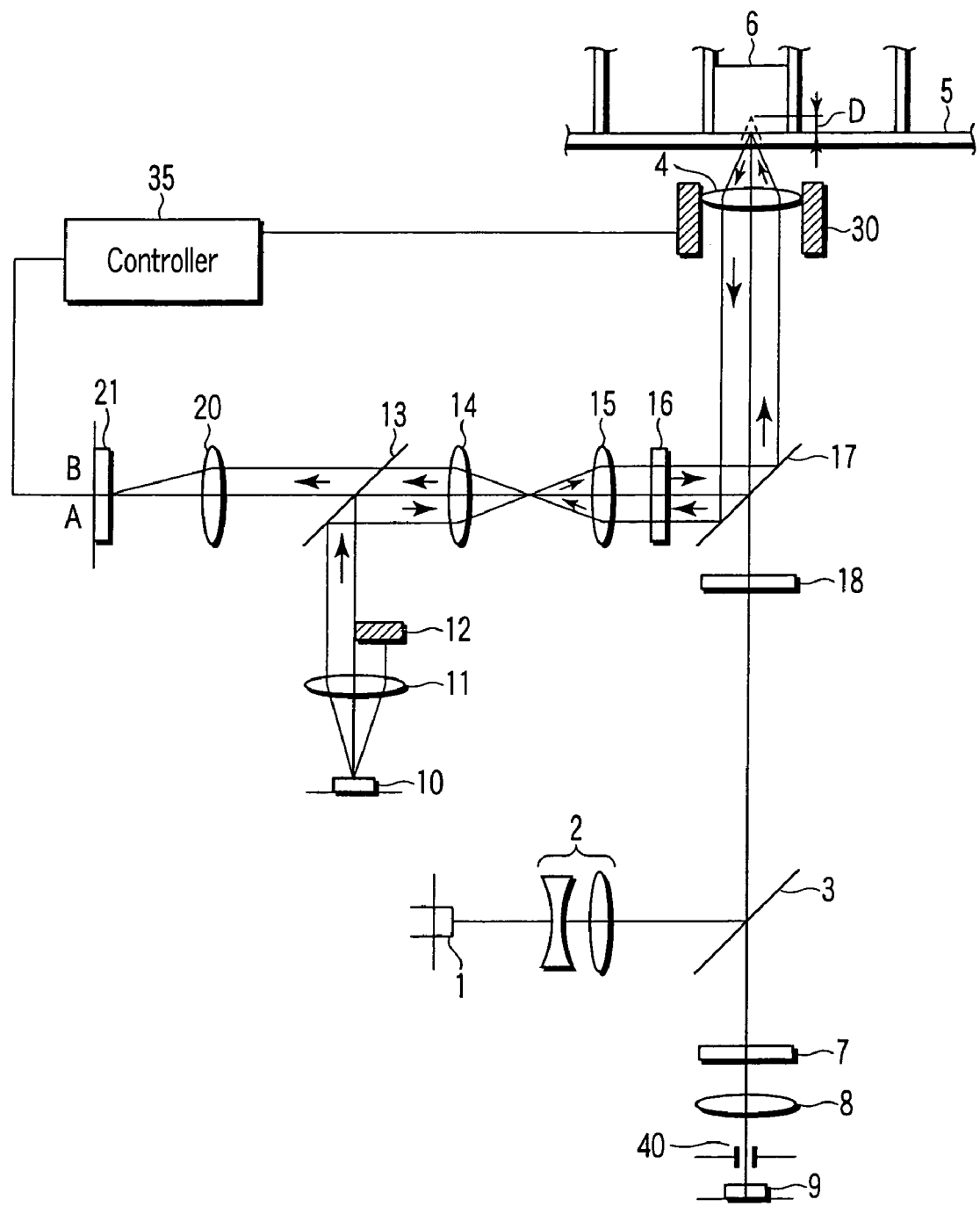
F I G. 1

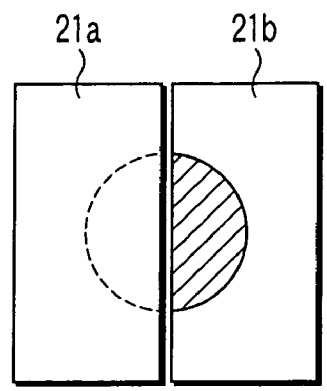
F I G. 4A
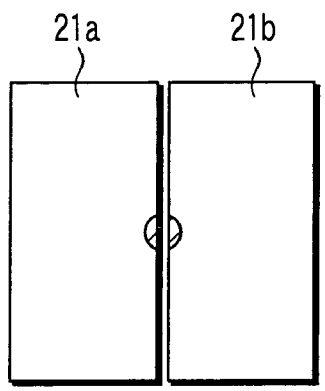
F I G. 4B
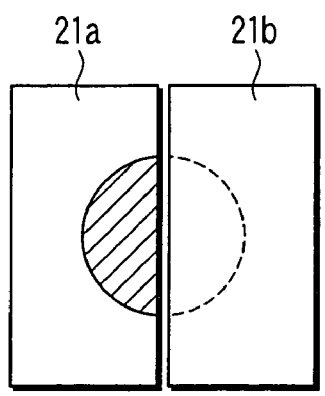
F I G. 4C

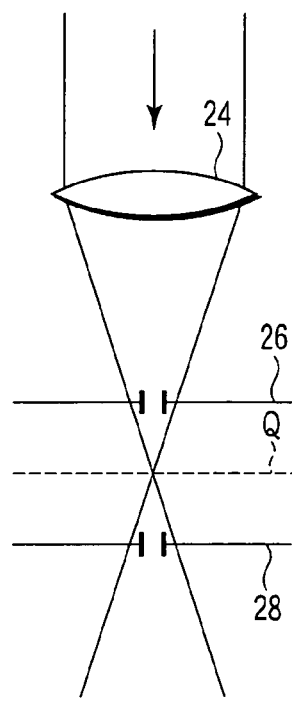
F I G. 10B
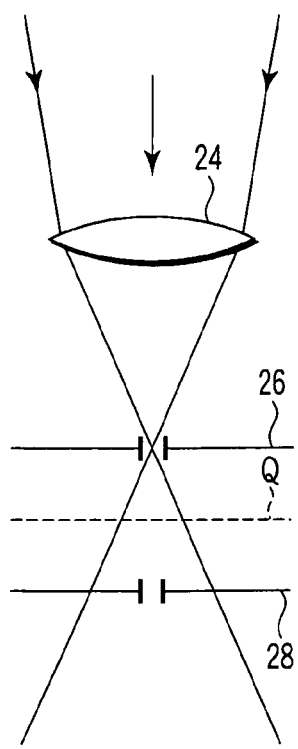
F I G. 10C

MEASURING APPARATUS

CROSS REFERENCE TO RELATED APPLICATIONS

This is a Continuation Application of PCT Application No. PCT/JP2005/011293, filed Jun. 20, 2005, which was published under PCT Article 21(2) in Japanese.

This application is based upon and claims the benefit of priority from prior Japanese Patent Application No. 2004-182510, filed Jun. 21, 2004, the entire contents of which are incorporated herein by reference.

BACKGROUND OF THE INVENTION

1. Field of the Invention

The present invention relates to a measuring apparatus for executing, for example, fluorescence correlation spectroscopy (FCS) in which light is applied to a sample, and fluorescence emitted from a fluorescent material contained as an indicator in the sample, and more particularly, to a measuring apparatus with an alignment detection unit for focusing light on the sample.

2. Description of the Related Art

The basic technique of the present invention relates to FCS that utilizes a confocal laser scanning microscope. In FCS, protein or colloidal particles labeled by a fluorescent material are floated in a solution within the viewing field of a confocal optical microscope, and a laser beam is applied to the fluorescent material to excite it, thereby analyzing variations in the intensity of fluorescence based on the Brownian motion of the fine particles to acquire a auto-correlation function and detect the number of target fine particles or translational diffusion speed of them.

For instance, Jpn. PCT National Publication No. 11-502608 discloses a method and apparatus in which a laser beam is applied by confocal laser scanning microscope to a sample labeled with a fluorescent material and placed on a sample stage, thereby analyzing variations in the intensity of fluorescence emitted from the sample, and detecting, for example, a statistical property, such as a translational diffusion coefficient, of fluorescent molecules, or the interaction of the molecules.

Further, U.S. Pat. No. 6,071,748 discloses an apparatus for condensing a laser beam onto a sample that contains a fluorescent material, and measuring the intensity or life of fluorescence emitted therefrom.

In methods for applying a laser beam to a sample to excite a fluorescent material contained therein, and analyzing fluctuation in the intensity of fluorescence emitted from the sample, a sample container called a microplate is often used. If a microplate is used, a large number of samples can be simultaneously received in a plurality of wells formed in the plate, and be measured individually. Further, since an extremely small amount of sample material of a microliter order can be measured, it is not necessary to prepare a large amount of sample material.

In fluorescence correlated spectroscopy, the bottom of a microplate is formed of, for example, glass, and an objective lens is located below the microplate. The light from a light source is applied to a sample contained in each well of the microplate through the bottom thereof, thereby detecting the behavior of each molecule of the sample. When a microplate with a transparent bottom is used, an optical signal, such as a fluorescence signal, generated by the sample can be measured by an excitation optical system. Namely, a measuring device of a simple structure can be used, which is advantageous in designing the device.

Further, when a light beam is directly condensed onto a sample in each well through the bottom of the microplate, it is necessary to accurately adjust the focal point of the beam to reliably guide it to the sample. However, since an objective lens of high magnification is used as a condensing lens, the focal depth is extremely shallow. In this condition, to accurately adjust the focal point, a skilled operator is needed.

To solve this problem, the following techniques, for example, have been proposed.

Jpn. PCT National Publication No. 2002-541430 discloses a technique of detecting the position of the bottom of a microplate simply using a measuring optical system. Namely, the light from a light source is condensed onto a sample through the microplate bottom, and the focal point of the incident light is gradually moved along the optical axis, thereby measuring the intensity of the light directly reflected from the microplate bottom. The position on the optical axis, at which the intensity peak value is detected, is determined to be the bottom of the microplate, and the focal point of light in each well of the microplate is set based on the determination result.

Jpn. PCT National Publication No. 2002-542480 discloses a technique of receiving, by a CCD camera, the beam emitted from a light source, detecting the position of the beam spot on the light-receiving surface of the camera to determine, for example, the bottom position of the plate, and adjusting the focal point of the light source in accordance with the detected bottom position.

Jpn. Pat. Appln. KOKOKU Publication No. 02-59963 discloses a technique of detecting a deviation in the focal point of a sample, based on a deviation in the point, on the light-receiving surface of a differential diode, of the light emitted from a light source, thereby moving a sample stage along the optical axis, based on the detected deviation, in order to converge the light spot of the light source on the surface of the sample.

BRIEF SUMMARY OF THE INVENTION

A measuring apparatus according to a first aspect of the present invention includes: a measuring apparatus which applies light, emitted from a light source, to a sample contained in a container, and detects light emitted from the sample to measure physical or chemical properties of the sample, comprising: a measuring optical system which measures the sample; and a position detection optical system which detects a position of a bottom of the container.

BRIEF DESCRIPTION OF THE SEVERAL VIEWS OF THE DRAWING

FIG. 1 is a view illustrating the configuration of a measuring apparatus according to a first embodiment of the invention;

FIG. 4A is a view illustrating a light condensing point on the two-piece light-receiving element;

FIG. 4B is a view illustrating another light condensing point on the two-piece light-receiving element;

FIG. 4C is a view illustrating yet another light condensing point on the two-piece light-receiving element;

FIG. 10B is a view illustrating emission of light to pinholes;

FIG. 10C is a view illustrating emission of light to pinholes;

DETAILED DESCRIPTION OF THE INVENTION

Figure 2:
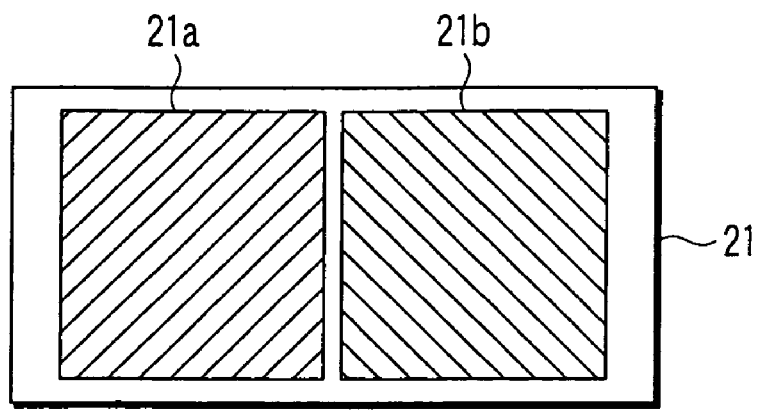
FIG. 2 is a view illustrating the structure of a two-piece light-receiving element.

The basic idea of the present invention will firstly be described.

In the prior art, as described above, the position detection operation for detecting the predetermined position is executed, and then the position adjustment operation for adjusting the focal point is executed based on the detection result, thereby performing focusing. Therefore, if an apparatus can be developed in which the execution of the position detection operation directly results in the position adjustment operation, the focusing operation can be speeded up.

Further, when a liquid sample is a measurement target, the position adjustment operation cannot be realized by directly detecting the light reflected from the liquid sample. However, if an apparatus can be developed in which a position adjustment operation concerning the liquid sample is realized by detecting the position of a container that contains the liquid sample, the focusing operation concerning the liquid sample can also be speeded up.

Embodiments of the invention, constructed based on the above ideas, will now be described.

Note that in the invention, the term "beam-condensing optical system" means an optical system with a function for condensing a light beam using a lens.

First Embodiment

FIG. 1 is a view illustrating the configuration of a measuring apparatus according to a first embodiment of the invention. In this measuring apparatus, an alignment detection optical system and measuring optical system are configured to include different optical paths.

Firstly, the configuration and operation of the measuring optical system will be described.

A light source 1 is formed of an argon laser with a wavelength of 488 nm. The argon laser generates a laser beam for exciting a sample. The measurement beam emitted from the light source 1 is converted by a beam expander 2 into a parallel light beam with an enlarged diameter. The resultant measuring means is reflected by a dichroic mirror 3, and passed through a filter 18 and dichroic beam splitter 17. After that, the resultant light is condensed by an objective lens 4.

An objective-lens drive mechanism 30 is provided around the objective lens 4. The objective-lens drive mechanism 30 holds the objective lens 4, and is used to move it along the optical axis manually or via a controller 35. As a result, the light-condensing position (focal point) of the measurement beam is adjusted.

The condensed measurement beam is passed through the bottom of a microplate 5 and focused in a sample solution contained in each well. The focal point is 10 μm above the bottom of each well of the microplate 5, i.e., the upper surface of the bottom of the microplate 5 serving as the bottom of each well. A sample 6 indicated by a fluorescent material is contained in each well of the microplate 5, and emits fluorescence when it is excited by the measurement beam. Rhodamine green (RhG), for example, is used as the fluorescent material.

The fluorescence emitted from the sample contained in each well is passed through the dichroic beam splitter 17 and filter 18 via the objective lens 4. The dichroic beam splitter 17 has the property of transmitting therethrough the measurement beam and fluorescence, and the filter 18 has the property of interrupting an alignment detection laser beam, described later.

Subsequently, the fluorescence is passed through a dichroic mirror 3, then through a filter 7 that passes only fluorescence, and is condensed by a condensing lens 8 into a pinhole 40. The fluorescence having noise generated in each well and erased by the pinhole 40 is received by a photodetector 9 provided behind the pinhole 40, where it is converted into a measurement signal.

The configuration and operation of the alignment detection optical system will be described.

An alignment detection beam emitted from an alignment detection laser 10 having a polarization property is converted into a parallel beam by a collimator lens 11, and a half of the beam spot is shaded by a shading plate 12 provided across the optical path. At this time, the beam has a substantially semicircular section. The remaining half of the beam is reflected by a polarization beam splitter 13, then condensed by a lens 14, and passed through a relay lens 15 and ¼ wavelength plate 16, with the result that the beam, linearly polarized, is converted into a circularly polarized beam.

The resultant beam is reflected by a dichroic beam splitter 17, and then converged by the objective lens 4 on the upper surface of the bottom of the microplate 5. Subsequently, the beam is reflected by the bottom upper surface of the microplate 5, then passed through the objective lens 4, and further reflected by the dichroic beam splitter 17. When the beam is again passed through the ¼ wavelength plate 16, it is converted from a circularly polarized beam into a linearly polarized beam. The beam is then passed through the lens 15, converted into a parallel beam by the lens 14, and passed through the polarization beam splitter 13. The beam passing through the polarization beam splitter 13 is condensed by a lens 20, and then received by a two-piece light-receiving element 21 located at the focal point. Based on the output of the two-piece light-receiving element 21, a controller 35 drives the objective-lens drive mechanism 30 to move the objective lens 4 along the optical axis.

FIG. 2 is a view illustrating the structure of the two-piece light-receiving element 21. The two-piece light-receiving element 21 comprises two photoelectric conversion elements 21a and 21b formed of the same material and having the same shape. A description will be given of which portion of the two-piece light-receiving element 21 the beam condensed by the lens 20 is converged on.

Figure 3A:
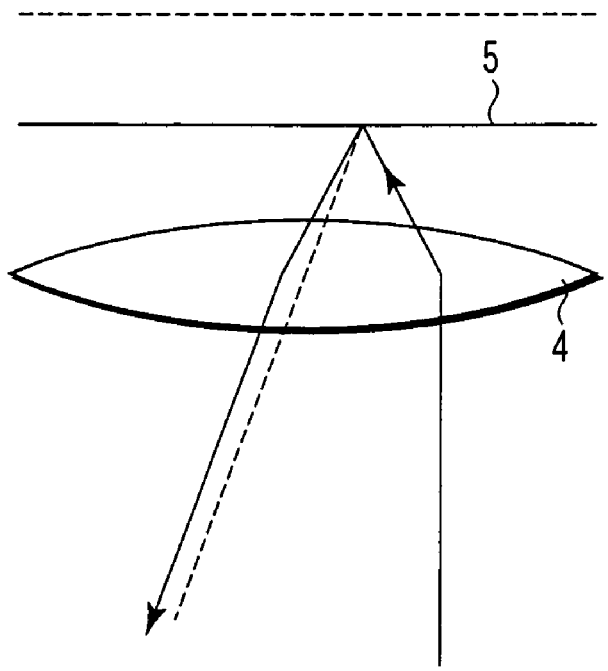
FIG. 3A is a view illustrating light reflection according to the distance between an objective lens and microplate.
Figure 3B:
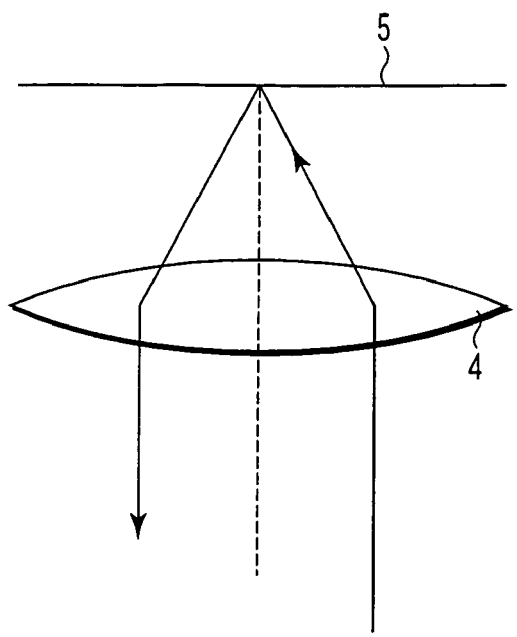
FIG. 3B is a view illustrating light reflection according to the distance between the objective lens and microplate.
Figure 3C:
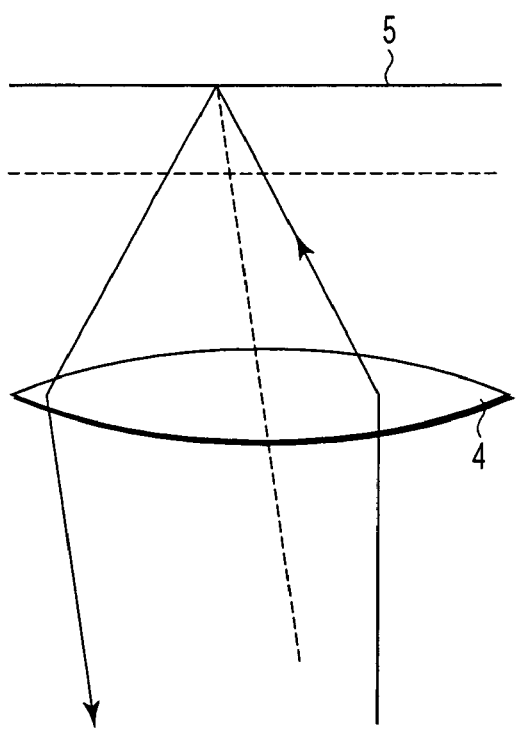
FIG. 3C is a view illustrating light reflection according to the distance between the objective lens and microplate.

FIGS. 3A, 3B and 3C are views each illustrating light reflection according to the distance between an objective lens and microplate.

When the distance between the objective lens 4 and the bottom surface of the microplate 5 is identical to a preset value, the reflected beam passes through a symmetrical portion of the objective lens 4 with respect to the axis of the lens, as shown in FIG. 3B. However, when the distance between the objective lens 4 and the bottom surface of the microplate 5 is less than the preset value, the reflected beam passes through a portion of the objective lens 4 close to the axis, as shown in FIG. 3A. Further, when the distance between the objective lens 4 and the bottom surface of the microplate 5 is more than the preset value, the reflected beam passes through a portion of the objective lens 4 away from the axis, as shown in FIG. 3C.

FIGS. 4A, 4B and 4C each show the light convergence position on the two-piece light-receiving element 21 according to the distance between the objective lens 4 and microplate 5.

When the distance between the objective lens 4 and the bottom surface of the microplate 5 is identical to a preset value, the reflected beam is equally guided to the photoelectric conversion elements 21a and 21b as shown in FIG. 4B. However, when the distance between the objective lens 4 and the bottom surface of the microplate 5 is more than the preset value, a greater part of the reflected beam is guided to the photoelectric conversion element 21a as shown in FIG. 4C. Further, when the distance between the objective lens 4 and the bottom surface of the microplate 5 is less than the preset value, a greater part of the reflected beam is guided to the photoelectric conversion element 21b as shown in FIG. 4A. Note that the beam spot size on the two-piece light-receiving element 21 varies according to the distance between the objective lens 4 and the bottom surface of the microplate 5.

Figure 5:
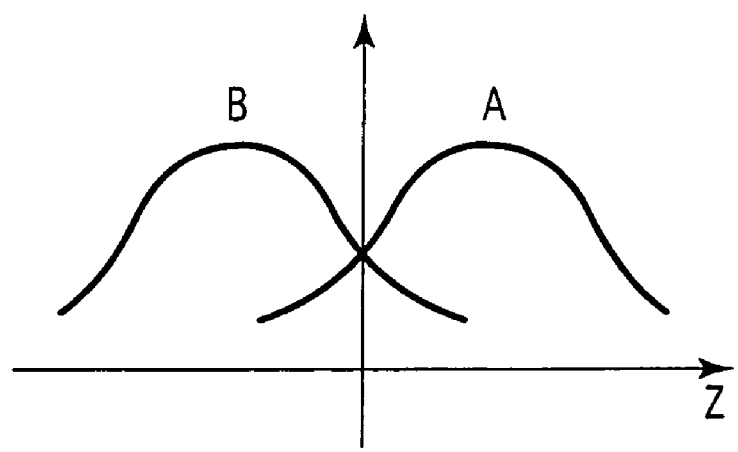
FIG. 5 is a view illustrating the outputs of two photoelectric conversion elements.

FIG. 5 shows the outputs A and B of the two photoelectric conversion elements 21a and 21b assumed when the objective lens 4 is moved along the optical axis.

When the distance between the objective lens 4 and the bottom surface of the microplate 5 is identical to a preset value, the outputs A and B are equal to each other. However, as the distance (Z) is increased, the output A increases. When the distance (Z) is further increased, only the output A is generated. Further, as the beam is deviated from the photoelectric conversion element 21a, the output A decreases. The same can be said of the output B.

Figure 6:
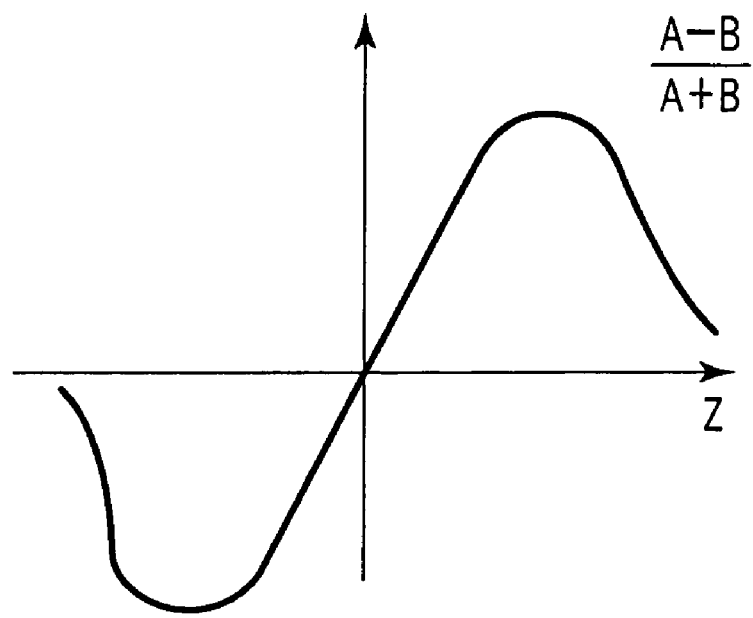
FIG. 6 is a view illustrating calculated signal of two photodetectors according to distance between objective lens and microplate.

Based on the outputs A and B, the controller 35 computes an alignment detection value $(A-B)/(A+B)$ as shown in FIG. 6. The controller performs feedback control to make the alignment detection value correspond to a deviation amount D by driving the objective-lens drive mechanism 30 to move the objective lens 4 along the optical axis. The alignment detection value indicates the distance between the objective lens 4 and the bottom surface of the microplate 5. As a result of this operation, the distance between the objective lens 4 and the bottom surface of the microplate 5 is controlled to the preset value.

Figure 7:
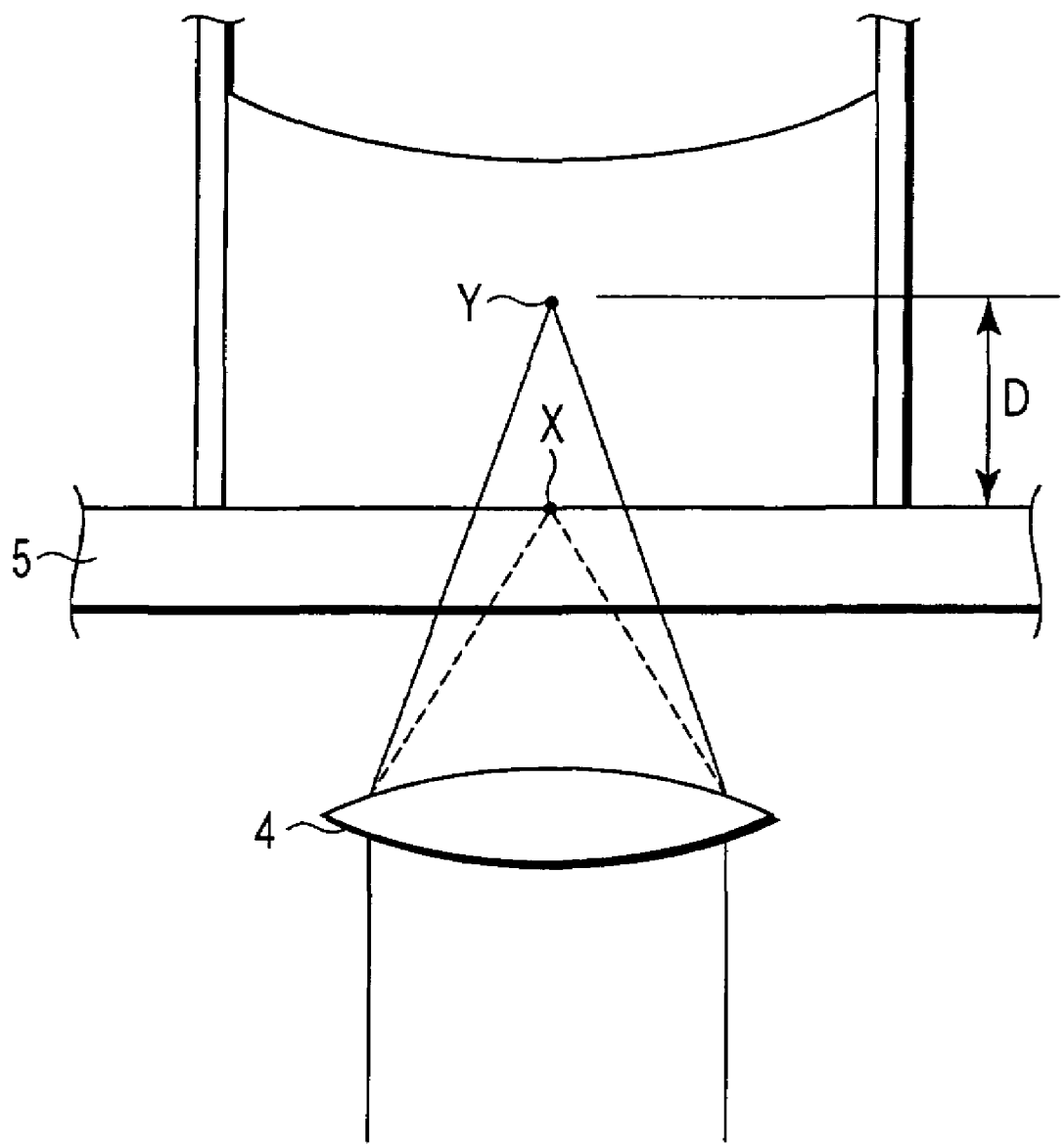
FIG. 7 is a view illustrating the result of an operation.

The result of the above operations is shown in FIG. 7. As shown in FIG. 7, the focal point (X) of the alignment detection laser is positioned on the bottom upper surface of the microplate 5. At this time, the focal point (Y) of the measuring laser is positioned above the focal point (X) of the alignment laser by the deviation amount D along the optical axis. Namely, the focal point (X) of the alignment laser and focal point (Y) of the measuring laser are beforehand adjusted so that they are deviated from each other by the preset amount D along the optical axis.

Methods for adjusting the deviation amount D will be described. It is desirable that the deviation amount D be adjusted to an appropriate value in accordance with the amount of a to-be-measured sample, and the type of the microplate 5, etc.

In a first adjustment method, an electrical offset value is imparted to the alignment detection value $(A-B)/(A+B)$ shown in FIG. 6, and the controller 35 performs control for making, zero, the offset alignment value. The electrical offset value is input by an external setting unit (not shown).

In a second adjustment method, the controller 35 adjusts, to an offset value, the alignment detection value $(A-B)/(A+B)$ shown in FIG. 6. The offset value as a control target value is input by an external setting unit (not shown).

In a third adjustment method, the alignment detection beam and measuring beam have different wavelengths. For instance, if an infrared laser beam is used as the alignment detection beam, the focal points of the alignment detection beam and measuring beam are made different because of the chromatic aberration of the objective lens 4, and the difference therebetween can be set as the deviation amount D.

A fourth adjustment method is a method for adjusting the optical system. In the alignment detection optical system, the deviation amount D can be adjusted by moving the condensing lens 14 along the optical axis. This is because the focal point of the alignment detection beam can be varied along the optical axis by moving the condensing lens 14. In light of this, a mechanism for moving the condensing lens 14 along the optical axis may be provided to adjust the deviation amount D. Further, the deviation amount D may be adjusted by moving the relay lens 15, shown in FIG. 1, along the optical axis, instead of moving the condensing lens 14 along the optical axis.

A fifth adjustment method is a method for adjusting the optical system. In this method, however, firstly, the beam convergence point on the microplate 15 is adjusted, and then the point (light-receiving point) of the two-piece light-receiving element 21 is adjusted accordingly.

Specifically, the beam convergence point is adjusted by guiding, to the objective lens 4, a beam more diffused or condensed than a collimated beam. To guide a condensed beam, the alignment detection laser 10 and collimator lens 11 may be moved away from each other. This operation provides the same advantageous effect as the operation of moving the relay lens 15 and condensing lens 14 away from each other.

After that, the light-receiving point is adjusted to the point corresponding to the deviation amount D adjusted by adjusting the light convergence point. In the above-mentioned case, the light-receiving point is adjusted by making the lens 20 and two-piece light-receiving element 21 close to each other in accordance with the deviation amount D.

The light convergence point and light-receiving point may be adjusted manually or automatically. For instance, software for adjusting the light convergence point and light-receiving point in the above-described manner when the deviation amount D is input may be created to operate the point driving device.

In the embodiment, the deviation amount D is set as 10 μm above the bottom upper surface of the microplate 5 in the sample solution. An argon laser with a wavelength of 488 nm or helium neon laser with a wavelength of 633 nm is used as the measuring laser. An infrared semiconductor laser with a wavelength of 780 nm, for example, is used as the alignment detection light source. However, the alignment detection light source is not limited to an infrared laser, but may be a laser of a visible light having a longer wavelength. Further, the alignment detection light source is not limited to a laser, but may be an LED. If an LED is used, the apparatus can be made compact and cheap. In the case of using an LED, efficient use of light can be realized by interposing a polarization plate between the collimator lens 11 and polarization beam splitter 13.

In addition, in the embodiment, a half of the beam spot of the alignment detection beam emitted from the alignment detection laser 10 is shaded by the shading plate 12 provided across the optical path. The resultant beam spot is substantially semicircular. However, since the portion of the beam around the axis has high intensity, it may be influenced by the diffraction of light due to the shading plate 12. Namely, in the semicircular beam spot, (1) the portion corresponding to the central portion of the original circular beam spot, and (2) the portion corresponding to the original circular beam spot portion around the centerline of the spot may well be influenced by diffraction. It is desirable to prevent the influence of diffraction.

FIGS. 13A, 13B, 13C and 13D show different shapes of the alignment detection beam.

Figure 13A:
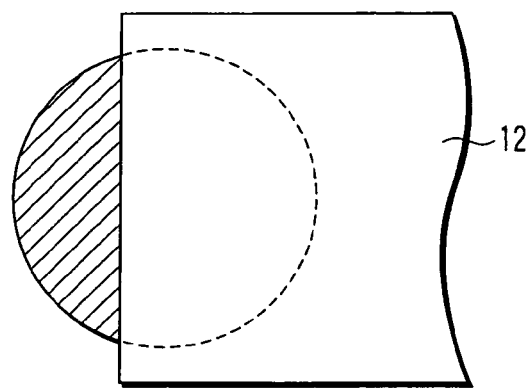
FIG. 13A is a view illustrating the shape of an alignment detection beam.
Figure 13B:
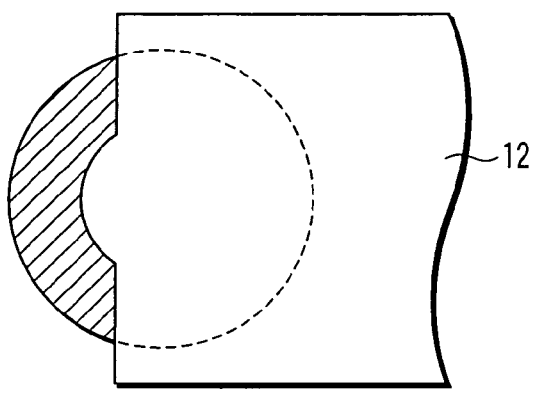
FIG. 13B is a view illustrating the shape of an alignment detection beam.
Figure 13C:
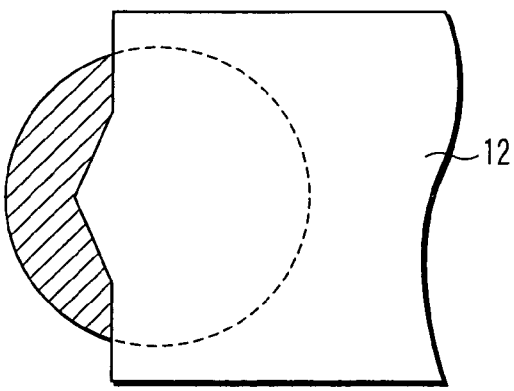
FIG. 13C is a view illustrating the shape of an alignment detection beam.
Figure 13D:
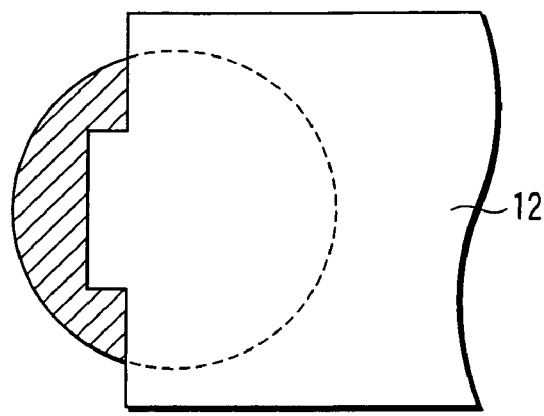
FIG. 13D is a view illustrating the shape of an alignment detection beam.

To solve the above-described problem, in the case of FIG. 13A, the shading plate 12 is moved to a position at which a greater part than the half of the beam is shaded. This can eliminate the influence of diffraction of a light beam of a strong intensity around the axis of the beam. In the case of FIG. 13B, the shape of the shading plate 12 is changed to shade the light near the axis. The shading plate 12 may have a triangular portion as shown in FIG. 13C, or a rectangular portion as shown in FIG. 13D.

Second Embodiment

Figure 8:
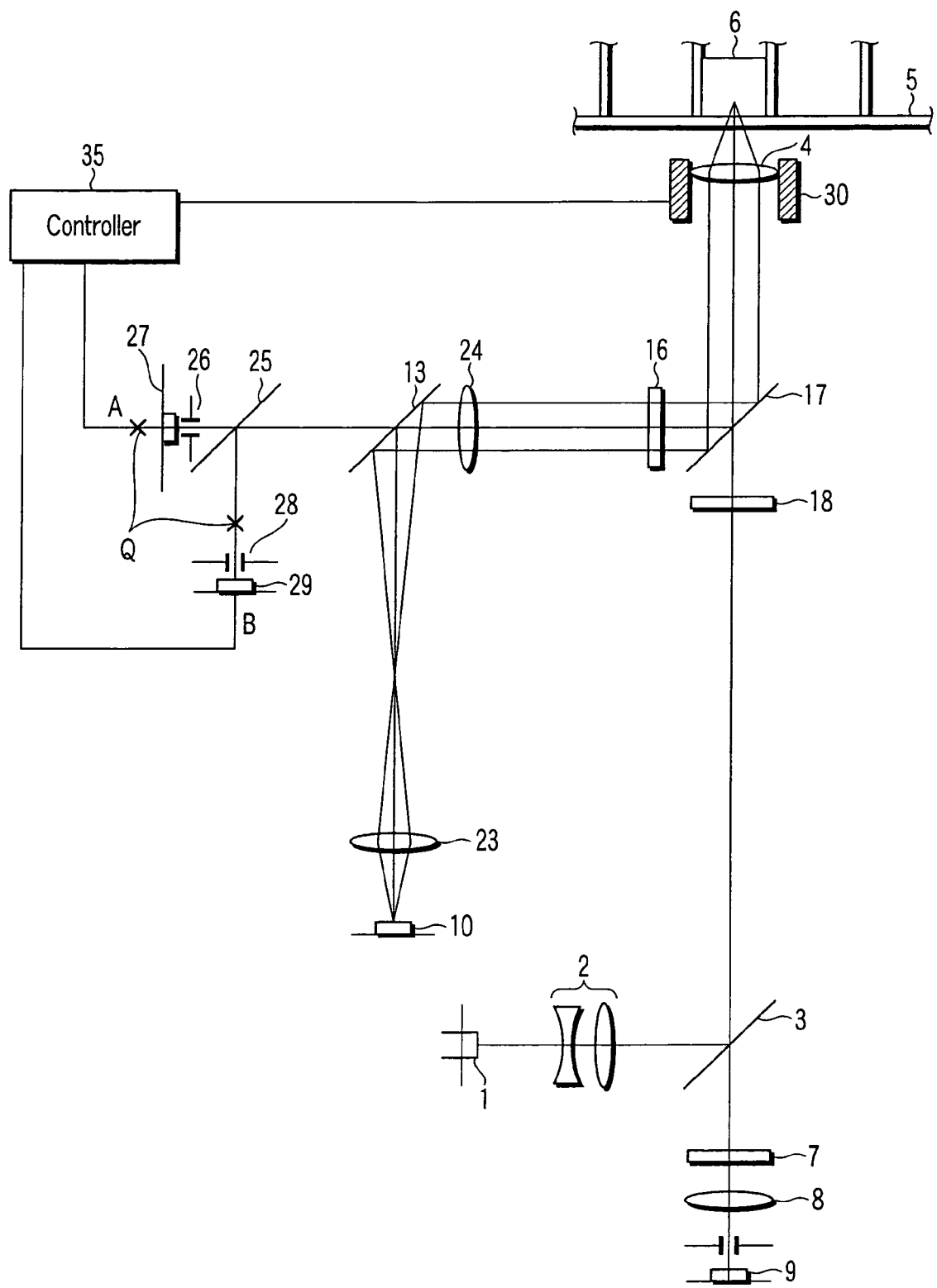
FIG. 8 is a view illustrating the configuration of a measuring apparatus according to a second embodiment of the invention.

FIG. 8 is a view illustrating the configuration of a measuring apparatus according to a second embodiment of the invention. The measuring apparatus of the second embodiment differs from the first embodiment in the configuration of the alignment detection optical system. Therefore, the elements similar to those in the first embodiment are denoted by corresponding reference numbers, and no detailed description is given thereof.

The configuration and operation of the alignment detection optical system will be described.

The alignment detection beam emitted from the alignment detection laser 10 is once converged by a beam expander 23, then again diverged, reflected by the polarization beam splitter 13, and collimated by a lens 24. The resultant beam, linearly polarized, is converted into a circularly polarized beam by the ¼ wavelength plate 16, and then reflected by the dichroic beam splitter 17.

The beam reflected by the dichroic beam splitter 17 is condensed by the objective lens 4 and guided to the microplate 5. The beam reflected from the bottom upper surface of the microplate 5 is again passed through the objective lens 24, where it is converted into a parallel beam. The parallel beam is reflected by the dichroic beam splitter 17, and passed through the ¼ wavelength plate 16, where it is converted from the circularly polarized beam to a linearly polarized one. The resultant beam is guided to the lens 24. The beam condensed by the lens 24 is passed through the polarization beam splitter 13 and guided to a beam splitter 25, where it is divided in two directions.

One of the beams is passed through a pinhole 26 provided before a focal point Q along the optical axis, and received by a photodetector 27. The photodetector 27, in turn, outputs an electrical signal A corresponding to the intensity of the received beam. The other beam is passed through a pinhole 28 provided after the focal point Q along the optical axis, and received by a photodetector 29. The photodetector 29, in turn, outputs an electrical signal B corresponding to the intensity of the received beam.

A description will be given of how the beam condensed by the lens 24 is guided to the pinholes 26 and 28.

Figure 9A:
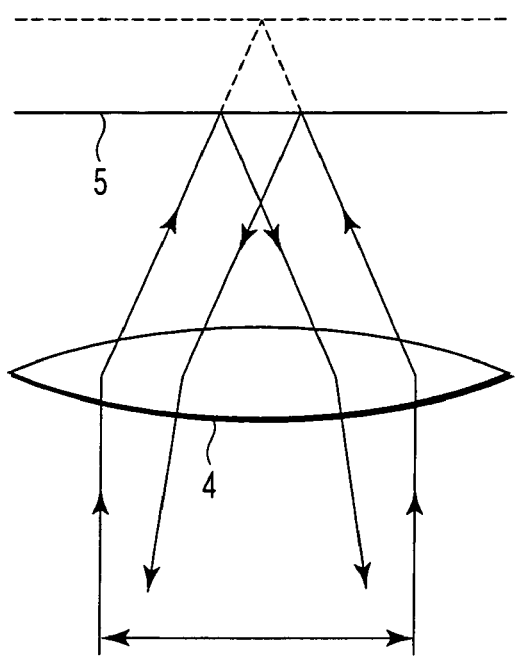
FIG. 9A is a view illustrating light reflection according to the distance between an objective lens and microplate.
Figure 9B:
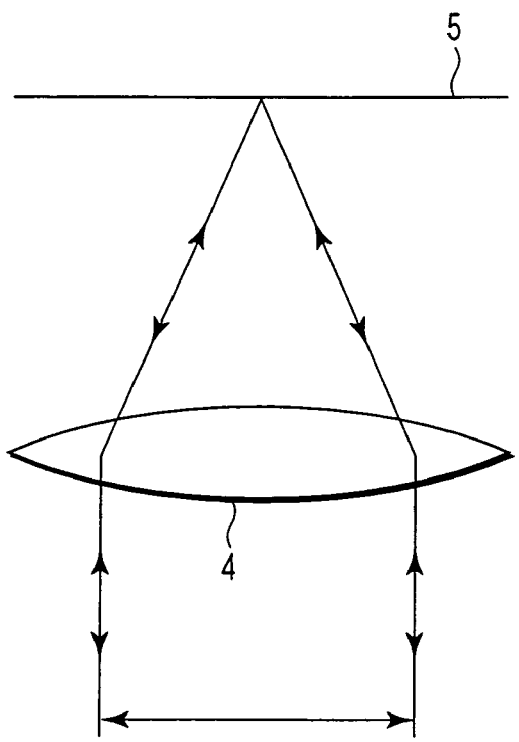
FIG. 9B is a view illustrating light reflection according to the distance between the objective lens and microplate.
Figure 9C:
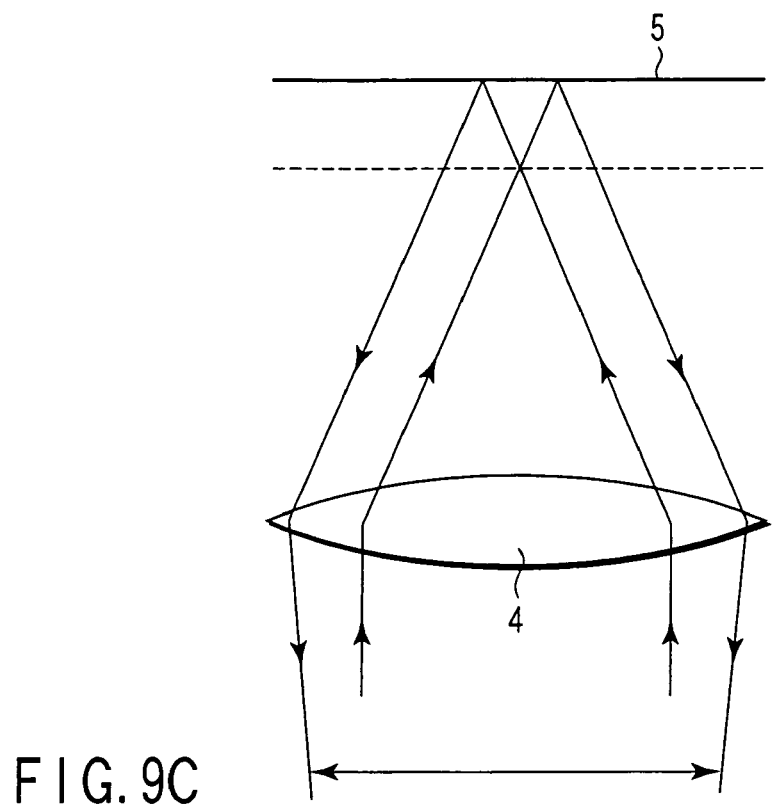
FIG. 9C is a view illustrating light reflection according to the distance between the objective lens and microplate.

FIGS. 9A, 9B and 9C each show light reflection according to the distance between the objective lens 4 and microplate 5.

When the distance between the objective lens 4 and the bottom surface of the microplate 5 is identical to a preset value (focal distance), the beam passing through the objective lens 4 is a parallel beam as shown in FIG. 9B. However, when the distance between the objective lens 4 and the bottom surface of the microplate 5 is less than the preset value, the beam passing through the objective lens 4 is a diverging beam as shown in FIG. 9A. Further, when the distance between the objective lens 4 and the bottom surface of the microplate 5 is more than the preset value, the beam passing through the objective lens 4 is a converging beam as shown in FIG. 9C.

Figure 10A:
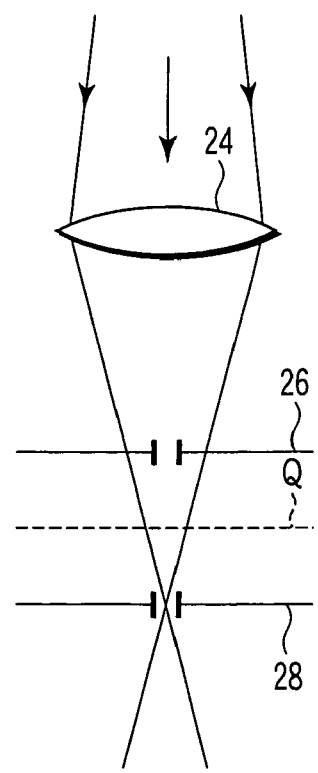
FIG. 10A is a view illustrating emission of light to pinholes.

FIGS. 10A, 10B and 10C each show emission of light to the pinholes 26 and 28 according to the distance between the objective lens 4 and microplate 5.

When the distance between the objective lens 4 and the bottom surface of the microplate 5 is identical to a preset value, the beam passing through the lens 24 is focused at the focal point Q and equally guided to the photodetectors 27 and 29, as is shown in FIG. 10B. However, when the distance between the objective lens 4 and the bottom surface of the microplate 5 is less than the preset value, the beam passing through the lens 24 is focused at the pinhole 28, and a greater part of the beam is guided to the photodetector 29, as is shown in FIG. 10A. Further, when the distance between the objective lens 4 and the bottom surface of the microplate 5 is more than the preset value, the beam passing through the lens 24 is focused at the pinhole 26, and a greater part of the beam is guided to the photodetector 27, as is shown in FIG. 10C.

Figure 11:
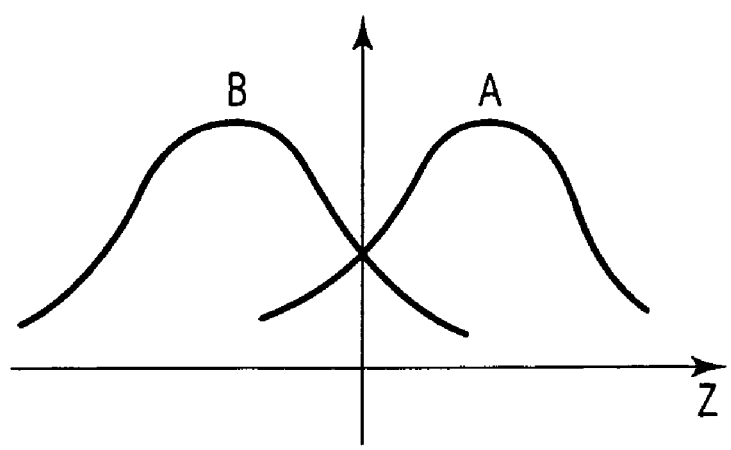
FIG. 11 is a view illustrating the outputs of two photodetectors.

FIG. 11 shows the outputs A and B of the two photodetectors 27 and 29 assumed when the objective lens 4 is moved along the optical axis.

When the distance between the objective lens 4 and the bottom surface of the microplate 5 is identical to a preset value, the outputs A and B are equal to each other. However, as the distance is increased, the output A increases. When the distance is further increased, the output A continues to assume a saturated state, and then decreases. The same can be said of the output B.

Figure 12:
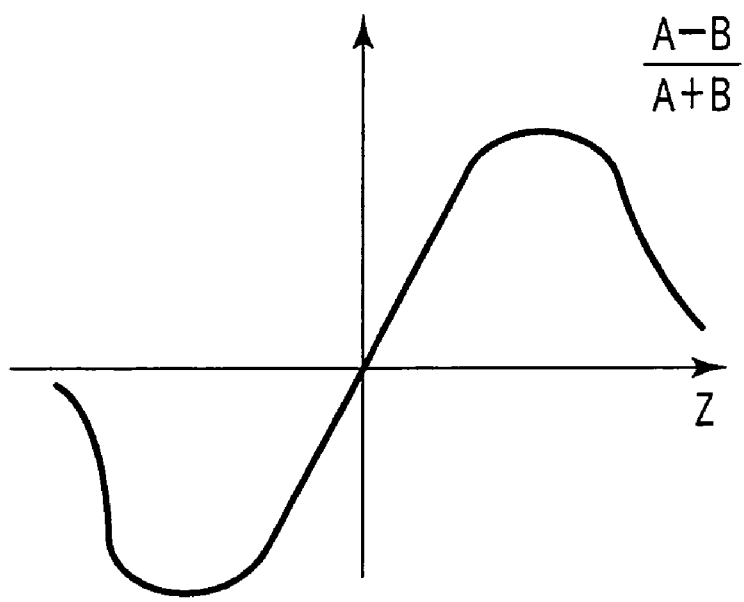
FIG. 12 is a view illustrating calculated signal of two photodetectors according to distance between objective lens and microplate.

Based on the outputs A and B, the controller 35 computes an alignment detection value (A−B)/(A+B) as shown in FIG. 12. The controller performs feedback control to make the alignment detection value correspond to a deviation amount D by driving the objective-lens drive mechanism 30 to move the objective lens 4 along the optical axis. As a result of this operation, the distance between the objective lens 4 and the bottom surface of the microplate 5 is controlled to the preset value.

In the second embodiment, the focal point (X) of the alignment detection laser and focal point (Y) of the measuring laser are beforehand adjusted so that they are deviated from each other by the preset amount D along the optical axis, as in the first embodiment. The deviation amount D can be adjusted by moving the lend 24 along the optical axis.

Third Embodiment

A measuring apparatus according to a third embodiment differs from the first embodiment in that an alignment optical system incorporated in the former is not a light condensing optical system. In the third embodiment, elements similar to those of the first embodiment are denoted by corresponding reference numbers, and no detailed description is given thereof.

Figure 14:
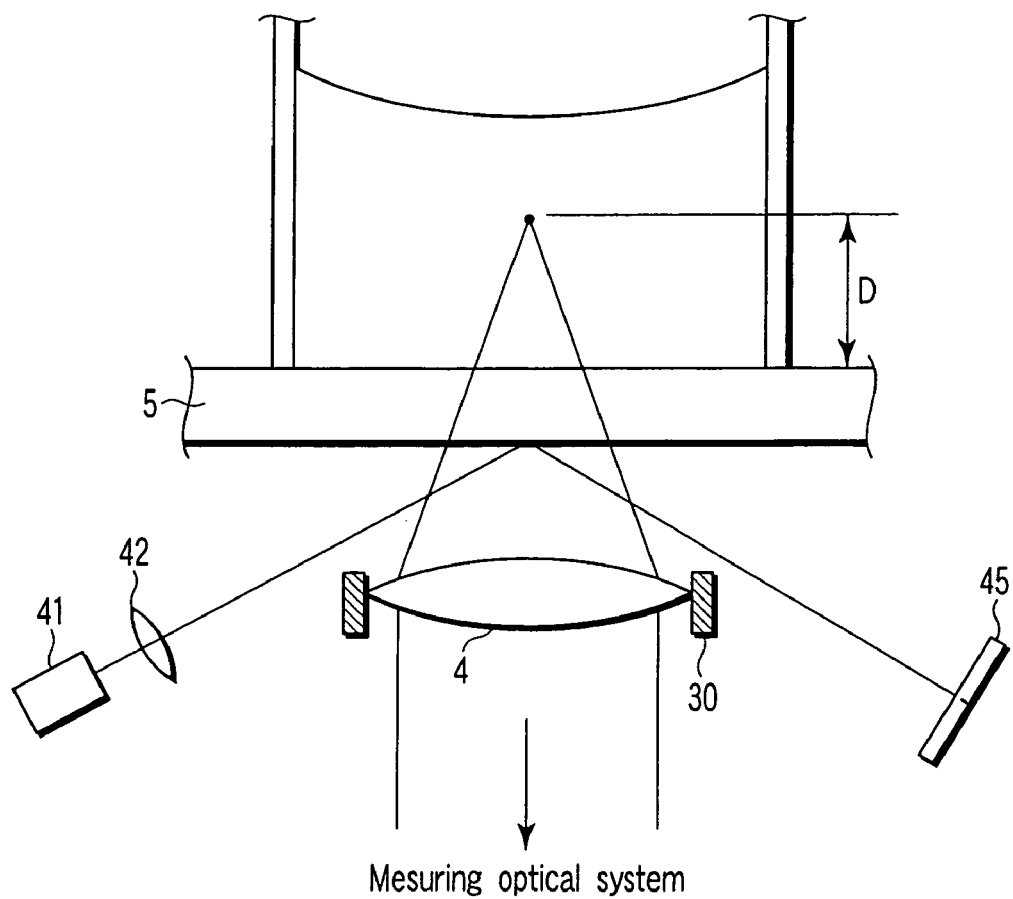
FIG. 14 is a view illustrating the positional relationship between an alignment optical system and measuring optical system.

FIG. 14 is a view useful in explaining the positional relationship between the alignment optical system and measuring optical system. FIG. 14 is an enlarged view of the objective lens 4, microplate 5 and their vicinity.

The alignment optical system comprises a light source 41, lens 42 and two-piece light-receiving element 45. The light source 41, lens 42 and two-piece light-receiving element 45 are formed integral with the objective lens 4, and the integral structure can be moved by the objective-lens drive mechanism 30 in the vertical direction (Z) of the figure. The alignment detection beam emitted from the light source 41 for alignment detection is converted into a parallel beam by the lens 42 and guided to the lower surface of the bottom of the microplate 5. The light reflected therefrom is guided to the two-piece light-receiving element 45 having two light-receiving surfaces.

Figure 15A:
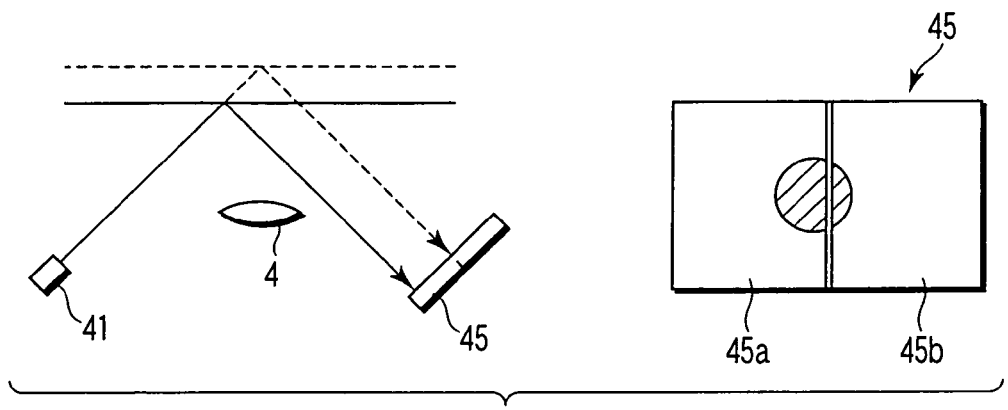
FIG. 15A is a view illustrating light reflection, and beam spots on the two-piece optical system, which accord to the distance between the objective lens and microplate.
Figure 15B:
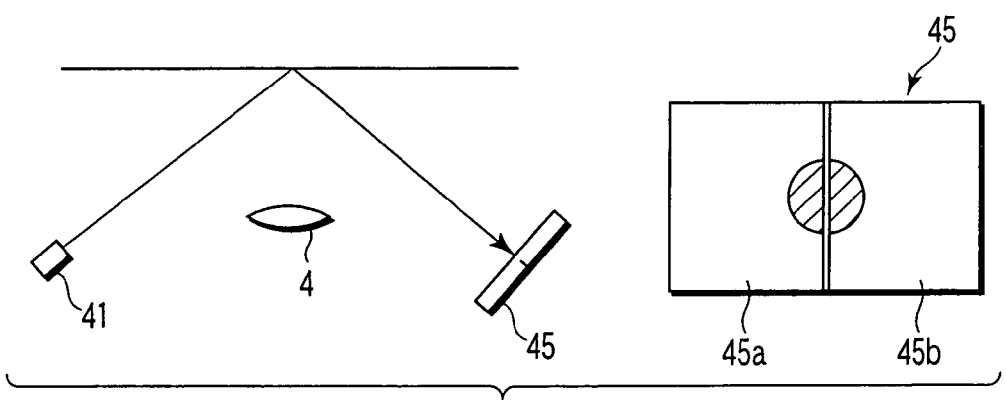
FIG. 15B is a view illustrating light reflection, and beam spots on the two-piece optical system, which accord to the distance between the objective lens and microplate.
Figure 15C:
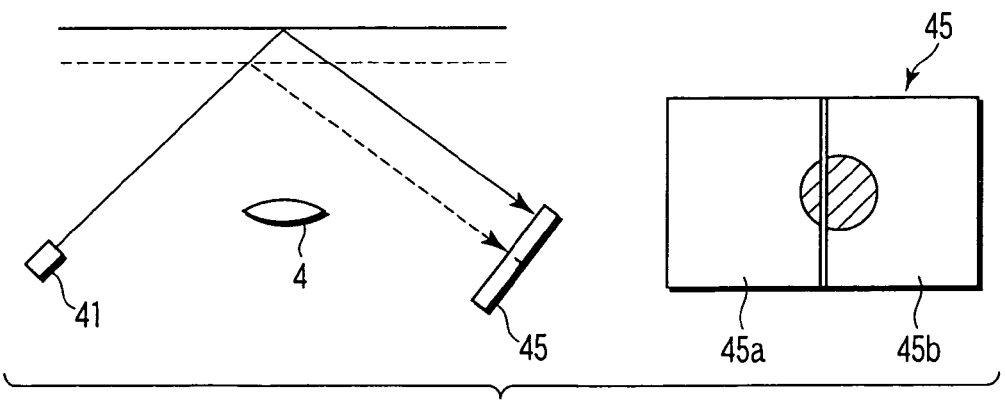
FIG. 15C is a view illustrating light reflection, and beam spots on the two-piece optical system, which accord to the distance between the objective lens and microplate.

FIGS. 15A, 15B and 15C each show light reflection and emission of light on the two-piece light-receiving element, according to the distance between the alignment optical system and microplate 5.

When the distance between the objective lens 4 and the bottom upper surface of the microplate 5 is identical to a preset value, the reflected beam is equally guided to the light-receiving elements 45a and 45b of the two-piece light-receiving element as shown in FIG. 5B. However, when the distance between the objective lens 4 and the bottom surface of the microplate 5 is less than the preset value, a greater part of the reflected beam is guided to the light-receiving element 45a of the two-piece light-receiving element as shown in FIG. 15A. Further, when the distance between the objective lens 4 and the bottom surface of the microplate 5 is more than the preset value, a greater part of the reflected beam is guided to the light-receiving element 45b of the two-piece light-receiving element as shown in FIG. 15C.

As in the first embodiment, an alignment detection value (A−B)/(A+B) as shown in FIG. 6 is computed based on the outputs A and B of the light-receiving elements 45a and 45b. Feedback control is performed to make the alignment detection value correspond to a preset value (e.g., 0) by driving the objective-lens drive mechanism 30 to move the alignment optical system and objective lens 4 along the optical axis. By this operation, the distance between the objective lens 4 and the bottom surface of the microplate 5 is controlled to the preset value. As a result, the focal point of the measuring optical system (not shown) can be controlled to a preset point in each well. The alignment detection beam may be guided to the bottom upper surface of the microplate 5.

When the detection beam is reflected from the bottom lower surface of the microplate 5, it is desirable to design so that the beam is not influenced by the light reflected from the bottom upper surface. The same can be said of the case where the beam is reflected from the bottom upper surface.

The present invention is not limited to the above-described embodiments. For instance, the same advantageous effect can be acquired if the ¼ wavelength plate 16 is not provided after the lens 15 but interposed between the polarization beam splitter 13 and dichroic beam splitter 17. Further, in FIG. 1, the condensing lens 14 is provided in the projection/reception common optical path. Instead of this structure, a lens for beam projection may be provided between the collimator lens 11 and polarization beam splitter 13, and a lens for beam reception be provided between the polarization beam splitter 13 and lens 20.

Further, the two-piece light-receiving element 21 or 45 may be replaced with a position sensitive detector (PSD), thereby directly detecting the position to which a light beam is applied. Furthermore, although each embodiment employs a single measuring laser, a measuring apparatus including a plurality of light-projecting systems and light-receiving systems may be constructed using a plurality of measuring lasers.

Also, the same advantageous effect can be acquired even if the focal point of the focus detection laser is set on the bottom lower surface of the microplate 5, instead of on the bottom upper surface of the microplate 5.

In addition, if it is not preferable to simultaneously perform the measuring operation and the focusing following operation as the operation of moving the objective lens along the optical axis, the focusing following operation may be performed when changing the well as a measurement target from one to another, and be stopped during the measurement operation.

The present invention is not limited to the above-described embodiments, but may be modified in various ways without departing from the scope. Various inventions can be realized by appropriately combining the structure elements disclosed in the embodiments. For instance, some of the disclosed structural elements may be deleted. Some structural elements of different embodiments may be combined appropriately.

The present invention can be widely used in the industrial field of manufacturing a measuring apparatus equipped with an alignment detection device that can quickly focus on a sample and is even applicable to a liquid sample.

What is claimed is:

1. A measuring apparatus which applies light, emitted from a light source, to a sample contained in a container, and detects light emitted from the sample to measure physical or chemical properties of the sample, comprising:

a measuring optical system which measures the sample; and a position detection optical system which detects a position of a bottom of the container, the measuring optical system comprising:

the light source for measurement;

a condensing lens which applies the light from the light source to the sample; and a measuring detector which detects the light emitted from the sample, the position detection optical system comprising:

a light source for position detection;

a collimate lens which converts light from the light source for position detection into parallel light;

a shading unit which shades substantially a half of a cross section of a luminous flux from the light source for position detection converted into the parallel light;

a guiding optical system which guides a remaining luminous flux passing through the shading unit as parallel light on a half surface of the condensing lens;

an image-forming lens which forms an image of the light applied via the condensing lens and reflected on a bottom of the container;

first and second detectors for position detection provided at a focal point position of the image-forming lens to receive the light of the image formed on the bottom of the container;

a calculating unit which calculates an index corresponding to a distance between the condensing lens and the bottom of the container in accordance with output values from the first and second detectors for position detection; and a controller which controls the distance between the condensing lens and the bottom of the container to vary the index to a predetermined value.

2. The apparatus according to claim 1, wherein any one of the first and second detectors for position detection receives a more quantity of light if the distance between the condensing lens and the bottom of the container is greater than the predetermined value, and the other detector receives a more quantity of light if the distance between the condensing lens and the bottom of the container is smaller than the predetermined value.

3. The apparatus according to claim 1, wherein the index I is represented in the following formula:

$$I=(A-B)/(A+B)$$

where the output values of the first and second detectors for position detection are represented by A and B, respectively.

4. The apparatus according to claim 1, wherein the shading unit shades an area which includes more than a half area of the cross section of the luminous flux and includes a center of the cross section.

5. The apparatus according to claim 1, wherein the shading unit has a shape for shading light near an axis of the center of the cross section of the luminous flux.

6. A measuring apparatus which applies light, emitted from a light source, to a sample contained in a container, and detects light emitted from the sample to measure physical or chemical properties of the sample, comprising:

a measuring optical system which measures the sample; and a position detection optical system which detects a position of a bottom of the container, the measuring optical system comprising:

the light source for measurement;

a condensing lens which applies the light from the light source to the sample; and a measuring detector which detects the light emitted from the sample, the position detection optical system comprising:

a light source for position detection;

a collimate lens which converts light from the light source for position detection into parallel light;

a guiding optical system which guides the parallel light to the condensing lens;

an image-forming lens which forms an image of the light applied via the condensing lens and reflected on a bottom of the container;

first and second detectors for position detection provided before and after a focal point position of the image-forming lens to receive the light of the image formed on the bottom of the container;

a calculating unit which calculates an index corresponding to a distance between the condensing lens and the bottom of the container in accordance with output values from the first and second detectors for position detection; and a controller which controls the distance between the condensing lens and the bottom of the container to vary the index to a predetermined value.

7. The apparatus according to claim 6, wherein any one of the first and second detectors for position detection receives a more quantity of light if the distance between the condensing lens and the bottom of the container is greater than the predetermined value, and the other detector receives a more quantity of light if the distance between the condensing lens and the bottom of the container is smaller than the predetermined value.

8. The apparatus according to claim 6, wherein the index I is represented in the following formula:

$$I=(A-B)/(A+B)$$

where the output values of the first and second detectors for position detection are represented by A and B, respectively.

9. The apparatus according to claim 6, wherein the position detection optical system further comprises an optical element having a pin hole provided in front of each of the first and second detectors for position detection.

10. A measuring apparatus which applies light, emitted from a light source, to a sample contained in a container, and detects light emitted from the sample to measure physical or chemical properties of the sample, comprising:

a measuring optical system which measures the sample; and a position detection optical system which detects a position of a bottom of the container, the measuring optical system comprising:

the light source for measurement;

a condensing lens which applies the light from the light source to the sample; and a measuring detector which detects the light emitted from the sample, the position detection optical system being configured to be connected to the condensing lens, comprising:

a light source for position detection;

a guiding optical system which converts light from the light source for position detection into parallel light and applies the parallel light to a bottom of the container in an oblique direction;

first and second detectors for position detection which receive the light reflected on the bottom of the container;

a calculating unit which calculates an index corresponding to a distance between the condensing lens and the bottom of the container in accordance with output values from the first and second detectors for position detection; and a controller which controls the distance between the condensing lens and the bottom of the container to vary the index to a predetermined value.

11. The apparatus according to claim 10, wherein any one of the first and second detectors for position detection receives a more quantity of light if the distance between the condensing lens and the bottom of the container is greater than the predetermined value, and the other detector receives a more quantity of light if the distance between the condensing lens and the bottom of the container is smaller than the predetermined value.

12. The apparatus according to claim 10, wherein the index I is represented in the following formula:

$$I=(A-B)/(A+B)$$

where the output values of the first and second detectors for position detection are represented by A and B, respectively.

* * * * *